(12) United States Patent
Thakker et al.

(10) Patent No.: US 7,713,949 B2
(45) Date of Patent: May 11, 2010

(54) COMPOSITIONS AND METHODS FOR ENHANCING PARACELLULAR PERMEABILITY ACROSS EPITHELIAL AND ENDOTHELIAL BARRIERS

(75) Inventors: Dhiren R. Thakker, Raleigh, NC (US); Peter D. Ward, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 286 days.

(21) Appl. No.: 09/974,519

(22) Filed: Oct. 10, 2001

(65) Prior Publication Data

US 2002/0115641 A1 Aug. 22, 2002

Related U.S. Application Data

(60) Provisional application No. 60/239,328, filed on Oct. 10, 2000.

(51) Int. Cl.
| | | |
|---|---|---|
| A01N 57/00 | (2006.01) | |
| A61K 31/66 | (2006.01) | |
| A01N 57/26 | (2006.01) | |
| A61K 31/685 | (2006.01) | |
| A01N 33/12 | (2006.01) | |
| A01K 31/14 | (2006.01) | |

(52) U.S. Cl. ........................... 514/75; 514/76; 514/642; 514/946

(58) Field of Classification Search ................... 514/75, 514/76, 642, 946
See application file for complete search history.

(56) References Cited

U.S. PATENT DOCUMENTS

| | | | |
|---|---|---|---|
| 4,199,507 A | 4/1980 | Hoeksema | |
| 5,001,234 A | 3/1991 | Bundy et al. | |
| 5,144,045 A | 9/1992 | Wissner et al. | |
| 5,208,223 A | 5/1993 | Wissner et al. | |
| 5,234,933 A * | 8/1993 | Marnett et al. | 514/327 |
| 5,306,830 A | 4/1994 | Andersson et al. | |
| 5,326,902 A * | 7/1994 | Seipp et al. | 560/254 |
| 5,334,712 A | 8/1994 | Johnson et al. | |
| 5,360,815 A | 11/1994 | Fortin et al. | |
| 5,373,095 A | 12/1994 | Johnson et al. | |
| 5,430,050 A | 7/1995 | Ohtsuka et al. | |
| 5,519,163 A | 5/1996 | Gibbs et al. | |
| 5,580,956 A | 12/1996 | Saito et al. | |
| 5,942,246 A | 8/1999 | Mayhew et al. | |

FOREIGN PATENT DOCUMENTS

| | | |
|---|---|---|
| GB | 1511653 | 5/1978 |
| WO | WO 98/10776 | 3/1998 |
| WO | WO98/10776 A | 3/1998 |
| WO | 02 11666 A2 | 2/2002 |

OTHER PUBLICATIONS

Cereijido et al., Journal of Cell Science, 1993, Supplement 17, 127-132.*
Grunicke et al., Advan. Enzyme Regul., 1996, 36, 385-407.*
Bleasdale, J.E. et al., "Inhibition of Phospholipase C Dependent Processes by U-73,122," Advances in Prostaglandin, Thromboxane, and Leukotriene Research, p. 590-593, (Jul. 17, 1989).
Perrella, Frank W., et al., "Phospholipase C Inhibitors: A New Class of Cytotoxic Agents," J. Med. Chem., p. 2232-2237, (Jul. 17, 1994).
Cereijedo, M., et al., "The making of a tight junction," Journal of Cell Science, p. 127-132, (Jul. 17, 1993).
Tomita, Mikio et al., "Absorption-Enhancing Mechanism of Sodium Caprate and Decanoylcarnitine in Caco-2 Cells," The Journal of Pharmacology and Experimental Therapeutics, p. 739-743, (Jul. 17, 1995).
Lindmark, Tuulikki et al., "Absorption Enhancement through Intracellular Regulation of Tight Junction Permeability by Medium Chain Ftty Acids in Caco-2 Cells," The Journal of Pharmacology and Experimental Therapeutics, p. 362-369, (Jul. 17, 1998).
Wallach, Donald P., et al., "Studies on the Arachidonic Acid Cascade-I Inhibition of Phospholipase A2 in vitro and in vivo by Several Novel Series of Inhibitor Compounds," Biochemical Pharmacology, vol. 30 (No. 11), p. 1315-1324, (Jul. 17, 1981).
Liu et al., Dodecylphosphocholine-Mediated Enhancement of Paracellular Permeability and Cytotoxicity of Caco-2 Cell Monolayers, Journal of Pharmaceutical Sciences, 88(11):1161-1168 (Nov. 1999).
Pawelcyzk et al., Inhibition of Phospholipase Cδ by Hexadecylphosphorylcholine and Lysophospholipids with Antitumor Activity, Biochemical Pharmacology, 45(2):493-497 (1993).
Berkovic et al., Hexadecylphosphotylcholine Inhibits Phosphatidylinositol and Phosphatidylcholine Phospholipase C in Human Leukemia Cells, Journal of Experimental Therapeutics & Oncology, 1:302-311 (1996).
Grunicke et al., Inhibition of Phospholipase C and Protein Kinase C by Alkylphosphocholines, Drugs of Today, 34(F):3-14 (Dec. 1998).
Hashimoto et al., Effects of β-Lactoglobulin on the Tight-junctional Stability of Caco-2- SF Monolayer, Bioscience Biotechnol. Biochem., 62(9)1819-1821 (1998).
Cereijido et al., The Making of a Tight Junction, Journal of Cell Science, Suppl. 17:127-132 (1993).

(Continued)

Primary Examiner—Frederick Krass
Assistant Examiner—Benjamin Packard
(74) Attorney, Agent, or Firm—Jenkins, Wilson, Taylor & Hunt, P.A.

(57) ABSTRACT

Compositions and methods for enhancing paracellular permeability at an absorption site in a subject are disclosed. The method includes: (a) administering an effective amount of a phospholipase C inhibitor to a subject at a time in which enhanced paracellular permeability is desired; and (b) enhancing paracellular permeability in the subject at the absorption site through the administering of the effective amount of the phospholipase C inhibitor. The disclosed compositions and methods provide enhanced absorption of a hydrophilic drug in a subject.

5 Claims, 8 Drawing Sheets

OTHER PUBLICATIONS

Hilgard et al., Alkylphosphocholines: A New Class of Membrane-Active Anticancer Agents, *Cancer Chemotherapy and Pharmacology*, 32:90-95 (1993).

Hilgard et al., Inhibitors of Signal Transduction: The Alkylphosphocholines, *Drug News Perspectives*, 12(2):69-72 (Mar. 1999).

Ward et al., Phospholipase C-γ Modulates Epithelial Tight Junction Permeability Through Hyperphosphorylation of Tight Junction Proteins, *The Journal of Biological Chemistry*, 277(38):35760-35765 (Sep. 20, 2002).

Cereijido et al., Molecular Physiology and Pathyphysiology of Tight Junctions: I. Biogenesis of Tight Junctions and Epithelial Polarity, *American Journal of Physiology*, 279(3):G477-G482 (2000).

Gasbarrini et al., Structure and Function of Tight Junctions. Role in Intestinal Barrier, *Italian Journal of Gastroenterology and Hepatology*, 31(6):481-488 (Aug. 1999).

Perrella et al. Phospholipase C Inhibitors: A new class of cytotoxic agents. *Journal of Medicinal Chemistry*, vol. 37, (1994), pp. 2232-2237.

Lin et al. Influence of insecticide exposure on the in vivo and in vitro metabolic activity of rats. *Archives of Environmental Contamination and Toxicology*, vol. 2, No. 4, (1974), pp. 364-377.

Official Action corresponding Japanese Patent Application No. 2002-533851 dated Nov. 27, 2007.

Zheng et al. (1995) Effects of the Phospholipase-C Inhibitor, U73122, on Signaling and Secretion in Pituitary Gonadotrophs, *Endocrinology* 136(3):1079-1088.

Communication pursuant to Article 94(3) EPC corresponding to European Application No. 06119516.0-1223 dated Feb. 26, 2008.

Barros, F., et al., Modulation of human erg $K^+$ channel gating by activation of a G protein coupled receptor and protein kinase C. *The Journal of Physiology*. vol. 511, No. 2 pp. 333-346 (1998).

Official Action corresponding to Canadian Patent Application No. 2,425,215 dated May 22, 2008.

Official Action corresponding to European Patent Application No. 06 119 516.0-1223 dated Dec. 9, 2008.

Polascik, T., et al., Neomycin cannot be used as a selective inhibitor of inositol phospholipid hydrolysis in intact or semi-permeabilized human platelets. *Biochemical Journal*. vol. 243 pp. 815-819 (1987).

Sipma et al., Neomycin inhibits histamine and thapsigargin mediated $Ca^{2+}$ entry in $DDT_1MF-2$ cells independent of phospholipase C activiation. *European Journal of Pharmacology*, vol. 305, No. 1-3 pp. 207-212 (1996).

Van Itallie, C.M., and Anderson, J.M., Claudins and Epithelial Paracellular Transport. *Annual Review of Physiology*. vol. 68 pp. 403-429 (2006).

Van Itallie, C.M., and Anderson, J.M., The Molecular Physiology of Tight Junction Press. *Physiology*. vol. 19 pp. 331-338 (2004).

Ward et al., Role of Phospholipase C-β in the Modulation of Epithelial Tight Junction Permeability. *The Journal of Pharmacology and Experimental Therapeutics*. vol. 304 pp. 689-698 (2003).

Yeaman et al., Polarity of TRH receptors in transfected MDCK cells is independent of endocytosis signals and G protein coupling. *American Journal of Physiology*. vol. 270 pp. C753-C762 (1996).

Notice of Allowance corresponding to Canadian Patent Application No. 2,425,215 dated Apr. 17, 2009.

Correspondence summarizing Official Action corresponding to Japanese Patent Application No. 2002-533851 dated Jul. 1, 2008.

Kitagawa et al., Coumarin Derivatives for Medicinal Purposes. XIII. Hypothermal Action. (2), *Yakuqaku Zasshi*. vol. 79 pp. 639-643 (1959).

Mayer et al., The Relation between the Structure of Coumarin and its Derivatives, and their Activity as Germination Inhibitors. *Journal of Experimental Botany*. vol. 3 pp. 246-252 (1952).

Nicolaus, Symbiotic Approach to Drug Design. *Decision Making in Drug Research*. pp. 173-186 (1983).

Summons to attend oral proceedings pursuant to Rule 115(1) EPC corresponding to European Patent Application No. 06119516.0-1223/1754480 dated Sep. 16, 2009.

\* cited by examiner n= 8, 9, 10, 11, 12, 13, 14, 15, 16, 17, 18 or 19

$(CH_2)_n$, n=1 to 10

COMPOSITIONS AND METHODS FOR ENHANCING PARACELLULAR PERMEABILITY ACROSS EPITHELIAL AND ENDOTHELIAL BARRIERS

CROSS REFERENCE TO RELATED APPLICATIONS

This application is based on and claims priority to U.S. Provisional Application Ser. No. 60/239,328, filed Oct. 10, 2000, herein incorporated by reference in its entirety.

TECHNICAL FIELD

The present invention relates to compositions and methods for enhancing the bioavailability and brain penetration of a therapeutic agent. More particularly, the present invention pertains to compositions and methods for enhancing paracellular permeability to thereby enhance the bioavailability of a therapeutic agent in a subject.

| Table of Abbreviations | |
|---|---|
| TEER | transepithelial electrical resistance |
| SD | standard deviation |
| $EC_{10x}$ | concentration of paracellular permeability enhancing compound that increases mannitol flux by ten fold |
| $IC_{50}$ (PLC) | concentration of paracellular permeability enhancing compound that causes a fifty percent decrease in ATP-stimulated accumulation of [$^3$H]-inositol phosphates |
| MDCK | Madin Darby canine kidney |
| PLC | phospholipase C |
| SAR | structure activity relationship |
| $\Omega \cdot cm^2$ | ohms times square centimeters |
| $EC_{50}$ | concentration of paracellular permeability enhancing compound required to decrease TEER by fifty percent |
| U-73, 122 | N-alkylsuccinimido derivative of a steroid (structure provided in FIG 2B) |
| PKC | protein kinase C |
| MLCK | myosin light chain kinase |
| CNS | central nervous system |
| 3-NC | 3-nitrocoumarin |

BACKGROUND ART

Discovery and development of drugs that are orally bioavailable, in addition to being potent and selective, presents a major challenge to the pharmaceutical industry. Compounds that can easily partition into the lipid bilayer of the cell membrane are generally easily absorbed (transcellular route). In contrast, hydrophilic compounds are substantially unable to cross the cell membrane. Their passage across the epithelium via the intercellular route (paracellular route) is also severely restricted by the presence of intercellular junctions, known as tight junctions. Thus, the intestinal epithelium poses a significant barrier to absorption of orally administered hydrophilic therapeutic agents.

The tight junctions are highly specialized multi-protein complexes that are composed of both transmembrane and cytsolic proteins. Denkar, B. M. and Nigam, S. K. (1998) *Am. J. Physiol.* 274:F1-F9; Fanning, A. S., et al., *J. Soc. Nephrol.* 10:1337-1345 (1999). The opening of the tight junctions appears to be regulated by complex intracellular signaling mechanisms. Anderson, J. M., et al., *J. Cell Biol.* 106:1141-1149 (1998); Sakakibara, A., et al., *J. Cell. Biol.* 137:1393-1401 (1997). Many signaling pathways have been implicated in the regulation of paracellular permeability (e.g., tyrosine kinases, calcium, protein kinase C (PKC)). Anderson, J. M., and Van Italle, C. M., *Am. J. Phys.* 269:G467-G475 (1995); Collares-Buzato, C. B., et al., *Eur. J. Cell Biol.* 76:85-92 (1998); Mullin, J. M., et al., *Am. J. Physiol.* 275:C544-C554 (1998); Tai, Y. H., et al., *J. Membr. Biol.* 149:71-79 (1996). However, the molecular mechanisms associated with this regulation have not been thoroughly elucidated.

To date, several absorption-enhancing agents have been identified that improve the absorption of drug candidates across intestinal epithelium by modulation of tight junctions. However, most of these agents lack potency and selectivity for action on the tight junctions and thus, must be administered in amounts that produce millimolar (mM) in vivo concentrations. Such concentrations can lead to cytotoxicity and undesirable side effects. Additionally, their mechanism of action is unknown or poorly understood, and frequently, these agents act via multiple mechanisms. Hence, pharmaceutically acceptable absorption enhancers are not available for clinical use.

What is needed, then, is an absorption-enhancing agent that exhibits potency and selectivity for the enhancement of paracellular permeability. Further characterization of tight junction regulation and identification of agents that influence tight junction regulation thus represent long felt and continuing needs in the art.

SUMMARY OF THE INVENTION

A method of enhancing paracellular permeability at an absorption site in a subject is disclosed. The method comprises: (a) administering an effective amount of a phospholipase C inhibitor to a subject at a time in which enhanced paracellular permeability is desired; and (b) enhancing paracellular permeability in the subject at the absorption site through the administering of the effective amount of the phospholipase C inhibitor.

A method of enhancing absorption of a hydrophilic drug in a subject is also disclosed. The method comprises: (a) administering an effective amount of a phospholipase C inhibitor to the subject at a time prior to or in conjunction with administering the hydrophilic drug to the subject, whereby enhanced paracellular permeability is produced at an absorption site in the subject; and (b) enhancing absorption of the hydrophilic drug at the absorption site in the subject through the administering of the effective amount of the phospholipase C inhibitor.

A composition and a method of making the same are also disclosed. The formulation comprises: (a) a hydrophilic drug; (b) an effective amount of a phospholipase C inhibitor; and (c) a pharmaceutically acceptable carrier.

Accordingly, it is an object of the present invention to provide a novel composition and method for modulating paracellular permeability. The object is achieved in whole or in part by the present invention.

An object of the invention having been stated hereinabove, other objects will become evident as the description proceeds when taken in connection with the accompanying Figures and Laboratory Examples as best described herein below.

DETAILED DESCRIPTION OF THE INVENTION

Figure 1:
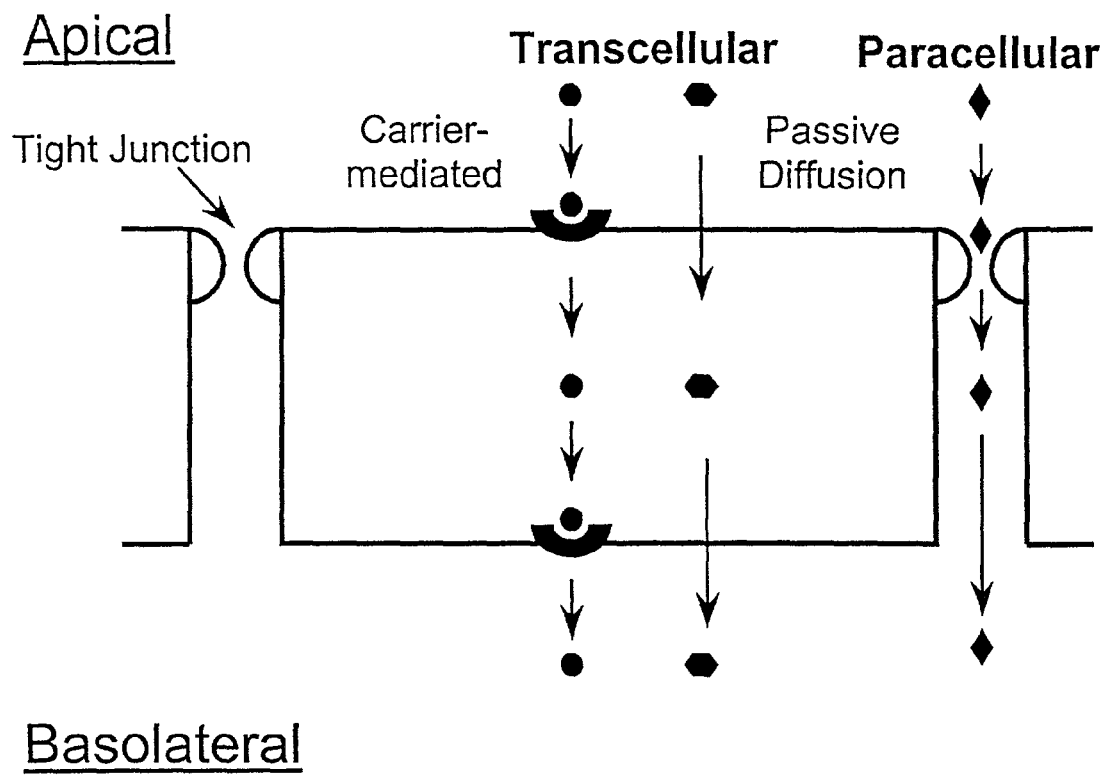
FIG. 1 is a schematic of transport across the intestinal epithelium. Molecules cross the intestinal epithelium into the blood primarily by three pathways, by passive diffusion across cell membranes (transcellular pathway); by passive diffusion between adjacent cells (paracellular pathway); or by carrier-mediated transport (carrier-mediated pathway).

Disclosed herein are novel absorption enhancers that act by modulating the paracellular permeability of intestinal epithelium via a previously uncharacterized mechanism—i.e., inhibition of the biological activity of the enzyme phospholipase C (PLC). In one embodiment, structure-activity relationships (SAR) were determined for the ability of alkylphosphocholines to increase paracellular permeability and inhibit PLC activity. The ability of alkylphosphocholines to increase paracellular permeability and inhibit PLC in Madin Darby canine kidney (MDCK) cells, an in vitro epithelial cell model for transport experiments, was significantly (p<0.05) correlated. To confirm the involvement of PLC inhibition in the regulation of paracellular permeability, selective PLC inhibitors (e.g., U-73,122 and 3-nitrocoumarin), whose ability to modulate tight junction permeability was unknown prior to the disclosure of the present invention presented herein, were evaluated for an ability to increase paracellular permeability as described in detail in the Laboratory Examples. These PLC inhibitors proved to be potent enhancers of paracellular (tight junction) permeability. Furthermore, the ability of the PLC inhibitors to increase paracellular permeability and inhibit PLC significantly (p<0.05) correlated with the ability of alkylphosphocholines to alter these parameters.

These results indicate that paracellular permeability can be increased by PLC inhibition. Thus, an inhibitor of the biological activity of the enzyme PLC (referred to herein as a "phospholipase C inhibitor" or as a "PLC inhibitor") can selectively increase paracellular permeability by modulation of tight junctions. Correspondingly, PLC inhibitors can be used as selective and potent absorption enhancers for hydrophilic drugs that are poorly absorbed across intestinal epithelium when administered orally. Three classes of compounds are preferred for use as absorption enhancers that act via PLC inhibition—alkylphosphocholines, 3-nitrocoumarins, and C-17 N-alkylsuccinimido derivatives of steroids.

Hydrophilic drugs that are in systemic circulation cannot enter the brain because of the presence of the "so called" blood-brain barrier. This barrier is formed by the highly specialized endothelium that lines the walls of the capillary supplying blood to the brain. The blood-brain barrier is also marked by the presence of tight junctions. In accordance with the present invention, PLC inhibitors can also serve as enhancers of central nervous system (CNS) penetration for hydrophilic compounds that cannot cross the blood-brain barrier easily.

A. DEFINITIONS

The following terms are believed to have well recognized meanings in the art. However, the following definitions are set forth herein to facilitate explanation of the present inventive subject matter.

As used herein and in the claims, the term "absorption site" is meant to refer to a site at which compounds, molecules or other substances are absorbed into the circulatory system or into the tissues of a subject. Indeed, an absorption site can include any site where tight junctions are presented and it is desirable to modulate paracellular permeability at the tight junction to facilitate absorption of a substance. Such substances can include drug compounds as well as endogenous compounds or molecules. Representative absorption sites include the intestinal epithelium, where absorption into the circulatory system occurs, and the highly specialized endothelium that lines the walls of the capillaries supplying blood to the brain, the so-called blood-brain barrier, where absorption into the tissues of the central nervous system (CNS) occurs.

As used herein and in the claims, the term "paracellular permeability" is meant to refer to the ability of a compound, molecule or other substance to pass through a tissue, such as the epithelial tissue that lines the intestine, via an intercellular route. Tight junctions are highly specialized multi-protein complexes that provide an effective barrier to molecules that are crossing the epithelium via a paracellular route. Despite ongoing efforts in the art, the regulation of tight junctions has not been well characterized. Thus, the characterization of an aspect of the regulation of tight junctions in accordance with the present invention meets a long-felt and continuing need in the art.

The term "hydrophilic drug" is meant to refer to a drug that is readily soluble in water and thus encounters difficulty in crossing the lipid bilayer of a cell membrane in a subject. The passage of such compounds across epithelial tissue via an intercellular route (i.e., a paracellular route) is also severely restricted by the presence of tight junctions.

As used herein and in the claims, the term "bioavailability" is meant to refer to an amount of an agent relative to the total dose administered, such as a therapeutic agent or drug, which is absorbed into the circulatory system of subject or into a tissue of a subject after administration as disclosed herein, e.g. oral, buccal, nasal, parenteral, rectal or transdermal administration, administration in a form suitable to contact colonic epithelium, or administration in a form suitable for inhalation or insufflation (either through the mouth or the nose) so as to contact, for example, pulmonary alveolar epithelium.

As used herein and in the claims, the terms "phospholipase C inhibitor" or "PLC inhibitor" are synonymous and refer to any substance, molecule or compound that has activity in the inhibition of a PLC enzyme, including but not limited to the currently identified isoforms of PLC, PLC-$\beta$ (beta) and PLC-$\gamma$ (gamma) as well as currently unknown PLC isoforms hereafter identified. While it is not applicants' desire to be bound by any particular theory of operation it is envisioned that a PLC inhibitor can act by direct inhibition of PLC or by indirect inhibition of PLC, such as via disruption of a G-protein coupled signaling pathway. Several representative PLC inhibitors are disclosed herein.

Following long-standing patent law convention, the terms "a" and "an" mean "one or more" when used in this application, including the claims.

B. GENERAL CONSIDERATIONS

Epithelial and endothelial sheets act as barriers to maintain distinct compartments within a multicellular organism, or subject. This is achieved by intercellular junctions that restrict the movement of large macromolecules, as well as to a lesser degree small molecules, between the epithelial cells or through the paracellular pathways. Even ion movement across the epithelium is attenuated, thus creating transepithelial electrical resistance (TEER). Paracellular leakage of macromolecules from one compartment to another is prevented by the formation of tight junctions. Diamond, J., "The Epithelial Junction: Bridge, Gate and Fence", *Physiologist* 20:10-18 (1977).

The barrier function of the tight junction is, however, not stagnant. For example, many hydrophilic nutrients easily cross the epithelium through the paracellular pathway. Ballard, S. T., et al., *Annu. Rev. Nutr.* 15:35-55 (1995). Therefore, the tight junction controls paracellular permeability in a dynamic fashion, suggesting that the epithelial cells have ability to regulate the function of the tight junction.

The tight junction is a complex structure that comprises both transmembrane and cytosolic proteins. Denkar, B. M. and Nigam, S. K. (1998) *Am. J. Physiol.* 274:F1-F9; Fanning, A. S., et al., *J. Soc. Nephrol.* 10:1337-1345 (1999). Many of these proteins (e.g., occludin, ZO-1, ZO-2 and ZO-3) are phosphorylated, suggesting that these proteins are the endpoints of various signal cascades. Anderson, J. M., et al., *J. Cell Biol.* 106:1141-1149 (1998); Sakakibara, A., et al., *J. Cell. Biol.* 137:1393-1401 (1997). Many signaling pathways have been implicated in the regulation of paracellular permeability (e.g., tyrosine kinases, calcium, protein kinase C (PKC). Anderson, J. M., and Van Italle, C. M., *Am. J. Phys.* 269:G467-G475 (1995); Collares-Buzato, C. B., et al., *Eur. J. Cell Biol.* 76:85-92 (1998); Mullin, J. M., et al., *Am. J. Physiol.* 275:C544-C554 (1998); Tai, Y. H., et al., *J. Membr. Biol.* 149:71-79 (1996). Until the disclosure of the present invention, molecular mechanisms associated with this regulation, however, have not been completely elucidated.

Molecules cross the intestinal epithelium into the blood in primarily three pathways, shown schematically in FIG. 1. First, molecules can cross by passive diffusion across the cell membranes (transcellular pathway); second by passive diffusion between adjacent cells (paracellular pathway); or third by carrier-mediated transport (carrier-mediated pathway). Lipophilic molecules easily cross the cell membrane via the transcellular route. On the other hand, hydrophilic molecules that are not recognized by a carrier cannot partition into the hydrophobic membrane, and thus must traverse the epithelial barrier via the paracellular pathway. The transport of hydrophilic molecules via the paracellular pathway, however, is severely restricted by the presence of the tight junctions.

Many useful therapeutic agents are hydrophilic and thus are not reliably delivered via the oral route, the most favored route of drug delivery. For example, the hydrophilic, broad-spectrum antibiotic cefoxitin has oral bioavailability of less than five percent in animals due to poor intestinal permeability and is currently only marketed as an IV formulation. Enalaprilat, an angiotensen converting enzyme inhibitor, is also poorly absorbed. This hydrophilic drug is also marketed as an IV formulation only.

C. THERAPEUTIC METHODS

A method of enhancing paracellular permeability at an absorption site in a vertebrate is provided in accordance with the present invention. In a preferred embodiment, the method comprises administering an effective amount of a PLC inhibitor to a subject at a time in which enhanced paracellular permeability is desired; and enhancing paracellular permeability in the subject at the absorption site through the administering of the effective amount of the PLC inhibitor.

In a more preferred embodiment, the PLC inhibitor is selected from the group including but not limited to an alkylphosphocholine, a 3-nitrocoumarin derivative, and an N-alkylsuccinimido steroid derivative. Optionally, the alkylphosphocholine can further comprise an alkyl chain of ten to twenty methylene groups, i.e. an alkyl chain of 10, 11, 12, 13, 14, 15, 16, 17, 18, 19, or 20 methylene groups. The absorption site preferably comprises intestinal epithelium. Alternatively, the absorption site can comprise the blood brain barrier.

A method of enhancing absorption of a hydrophilic drug in a subject is also disclosed. In a preferred embodiment, the method comprises administering an effective amount of a PLC inhibitor to the subject at a time prior to or in conjunction with administering a hydrophilic drug to the subject, whereby enhanced paracellular permeability is produced at an absorption site in the subject; and enhancing absorption of the hydrophilic drug at the absorption site in the subject through the administering of the effective amount of the phospolipase C inhibitor.

In a more preferred embodiment, the PLC inhibitor is selected from the group including but not limited to an alkylphosphocholine, a 3-nitrocoumarin derivative, and an N-alkylsuccinimido steroid derivative. Optionally, the alkylphosphocholine can further comprise an alkyl chain of ten to twenty methylene groups, i.e. an alkyl chain of 10, 11, 12, 13, 14, 15, 16, 17, 18, 19, or 20 methylene groups. The absorption site preferably comprises intestinal epithelium. Alternatively, the absorption site can comprise the blood brain barrier.

As used herein, an "effective" amount or dose refers to one that is effective or falls within an effective range in a majority of a population of subjects and that is sufficient to modulate PLC activity and/or to cause an improvement in absorption in a subject. Additionally, in accordance with the present invention, compounds that are selective and potent PLC inhibitors have been identified and the first evidence that such compounds can be used to modulate paracellular permeability has been provided. Thus, in accordance with the present invention, the compounds can be administered in dosages that provide for micromolar ($\mu M$) in vivo concentrations as opposed to millimolar concentrations. Representative in vivo concentrations can range from less than 1 $\mu M$ to about 100 $\mu M$, and can include intermediate concentrations, such as but not limited to 2, 4, 5, 10, 25, 50 or 75 $\mu M$. Thus, undesired side effects associated with non-specific activity and larger millimolar concentrations, e.g., cytotoxicity, are avoided with the methods and compositions of the present invention.

Thus, after review of the disclosure herein of the present invention, one of ordinary skill in the art choose an effective dose for a subject, taking into account the particular formulation and method of administration to be used with the composition as well as subject height, weight, severity of symptoms, and stage of the disorder to be treated.

A unit dose can be administered, for example, 1 to 4 times per day. Preferably, an effective amount of a PLC inhibitor is administered to the subject at a time prior to or in conjunction with administering a hydrophilic drug to the subject. In the case of administering the PLC inhibitor in conjunction with administering a hydrophilic drug to the subject it is preferred that the PLC inhibitor and the hydrophilic drug are administered to the subject in a single formulation. The dose depends on the route of administration and the formulation of a composition containing the compound or compounds. Further, it will be appreciated by one of ordinary skill in the art after reviewing the disclosure of the present invention that it might be necessary to make routine adjustments or variations to the dosage depending on the combination of agents employed, on the age and weight of the subject, and on the severity of the condition to be treated.

Such adjustments or variations, as well as evaluation of when and how to make such adjustments or variations, are well known to those of ordinary skill in the art of medicine. Evaluation parameters and techniques can vary with the subject and the severity of the disease. Particularly useful evaluative techniques include but are not limited to the assays disclosed in the Laboratory Examples presented herein.

The subject treated in the present invention in its many embodiments is desirably a human subject, although it is to be understood that the principles of the invention indicate that the invention is effective with respect to all vertebrate species, including mammals, which are intended to be included in the term "subject". In this context, a mammal is understood to include any mammalian species in which enhanced paracellular permeability is desirable, particularly agricultural and domestic mammalian species.

The methods of the present invention are particularly useful in the treatment of warm-blooded vertebrate animals. Therefore, the invention preferably pertains to mammals and birds.

More particularly, contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses (e.g. race horses). Also contemplated is the treatment of birds, including the treatment of those kinds of birds that are endangered, kept in zoos (e.g. ostriches), as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

D. PLC INHIBITOR COMPOUNDS

Figure 2A:
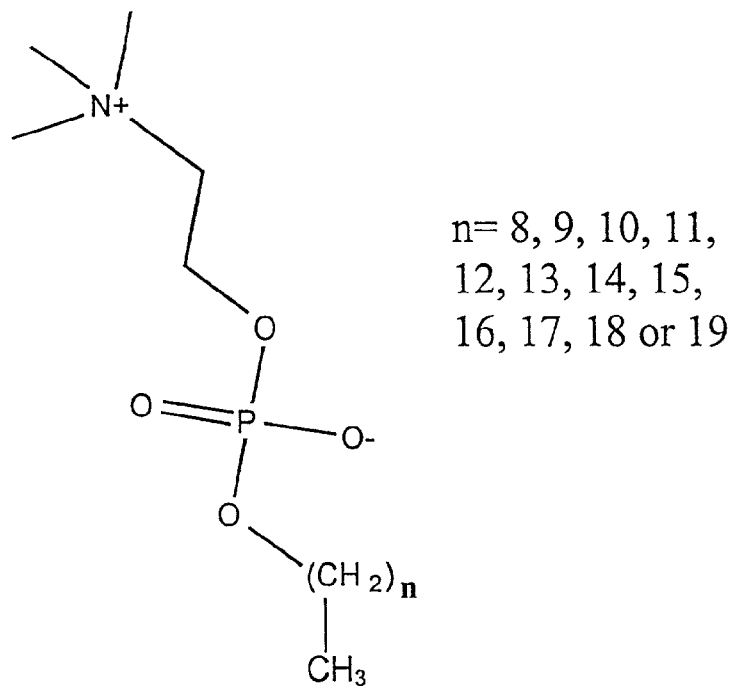
FIG. 2A is a structural formula, Formula 1, for the alkylphosphocholines prepared for structure activity relationships analysis in accordance with the present invention. Six alkylphosphocholines were synthesized or acquired that contained 10, 12, 14, 16, 18, or 20 methylene units in their alkyl chain, i.e. n=9, 11, 13, 15, 17 or 19. However, as shown in FIG. 2A, n can also be 8, 10, 12, 14, 16 or 18.

Preferred alkylphosphocholines include a compound of the Formula 2 as set forth in FIG. 2A, wherein n=8, 9, 10, 11, 12, 13, 14, 15, 16, 17, 18, 19 or 20. Representative phosphocholine synthesis techniques are disclosed in U.S. Pat. Nos. 5,208,223 and 5,144,045, the entire contents of each of which are herein incorporated by reference.

Hexadecylphosphocholine (C16) has been found to inhibit PLC in cellular and biochemical assays. Berkovic, D., et al., *J. Exp. Ther. Onc.* 1:302-311 (1996); Pawelcyzk, T. and Lowenstein, J. M., *Biochem. Pharm.* 45:493-497 (1999). C16, which has structural features including but not limited to a long alkyl chain and a zwitterionic functionality, was found to be very potent in causing an increase in paracellular permeability across MDCK cell monolayers. Thus, analogs of C16 were synthesized that varied in chain length by 10 to 20 methylene units (FIG. 2A, Formula 1). The potencies of these analogs were measured. An association between PLC inhibition and changes in paracellular permeability was clearly established.

Preferred 3-nitrocoumarins include 3-nitrocoumarin esters and ethers, wherein the ester or ether linkage is at the six-position of the 3-nitrocoumarin nucleus. Representative ether analogs include 7-hydroxy-heptanoxy-3-nitrocoumarin and 6-hydroxyhexaoxy-3-nitrocoumarin. Representative ester derivatives include heptanoyl and hexanoyl 3-nitrocoumarins. Other representative 3-nitrocoumarins are set forth in Table 1 below, and include 3-nitrocoumarin itself, 6-hydroxy-3-nitrocoumarin, 6-acetoxy-3-nitrocoumarin, 6-octanoyl-3-nitrocoumarin, 6-(10-undecenoyl)-3-nitrocoumarin and 6-(8-hydroxy-octanoxy)-3-nitrocoumarin. The derivatives can be synthesized using standard synthesis approaches, including but not limited to those disclosed in Perrella et al., *Journal of Medicinal Chemistry* (1994) 37 (14):2232-2237, herein incorporated by reference.

TABLE 1

Substituted 3-Nitrocoumarins (Formula 3)*

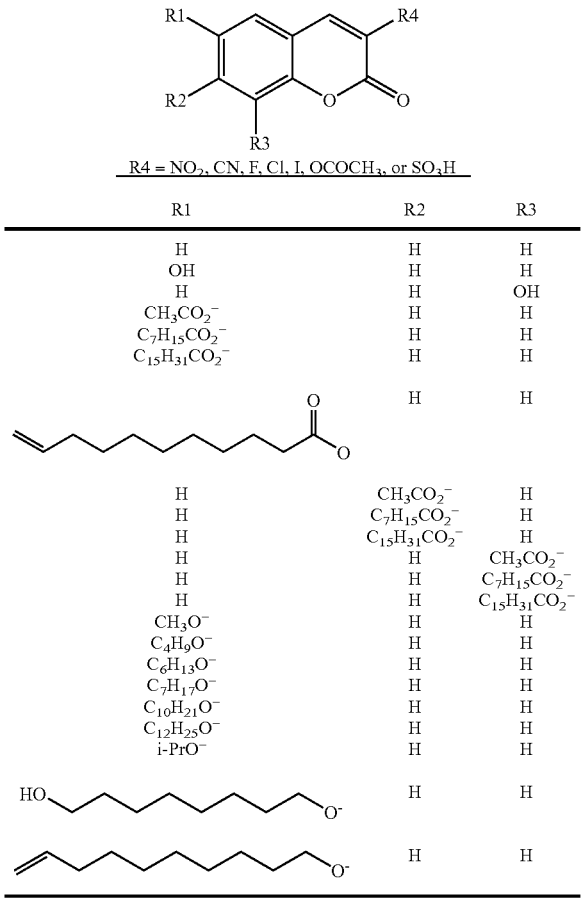

$R4 = NO_2, CN, F, Cl, I, OCOCH_3,$ or $SO_3H$

| R1 | R2 | R3 |
|---|---|---|
| H | H | H |
| OH | H | H |
| H | H | OH |
| $CH_3CO_2^-$ | H | H |
| $C_7H_{15}CO_2^-$ | H | H |
| $C_{15}H_{31}CO_2^-$ | H | H |
| CH2=CH-(CH2)7-C(O)O- | H | H |
| H | $CH_3CO_2^-$ | H |
| H | $C_7H_{15}CO_2^-$ | H |
| H | $C_{15}H_{31}CO_2^-$ | H |
| H | H | $CH_3CO_2^-$ |
| H | H | $C_7H_{15}CO_2^-$ |
| H | H | $C_{15}H_{31}CO_2^-$ |
| $CH_3O^-$ | H | H |
| $C_4H_9O^-$ | H | H |
| $C_6H_{13}O^-$ | H | H |
| $C_7H_{17}O^-$ | H | H |
| $C_{10}H_{21}O^-$ | H | H |
| $C_{12}H_{25}O^-$ | H | H |
| i-PrO$^-$ | H | H |
| HO-(CH2)8-O$^-$ | H | H |
| CH2=CH-(CH2)8-O$^-$ | H | H |

*In addition, same derivatives (exemplified in Table 1) of 3-cyanocoumarin, 3-halocoumarins (3-F, 3-Cl, 3-I), 3-acetoxycoumarin, and coumarin-3-sulfonic acid are also included. Thus, another substituent group, R4, is provided in accordance with the present invention at the 3 position in Formula 3 above, i.e. the carbon atom that is substituted by a nitro group above. Thus, R4 can comprise a nitro group (—NO₂), a cyano group (—CN), a halogen, such as —F, —Cl or —I, an acetoxy group, i.e., OCOCH₃⁻, or a sulfonic acid group, i.e. —SO₃H.

Figure 2B:
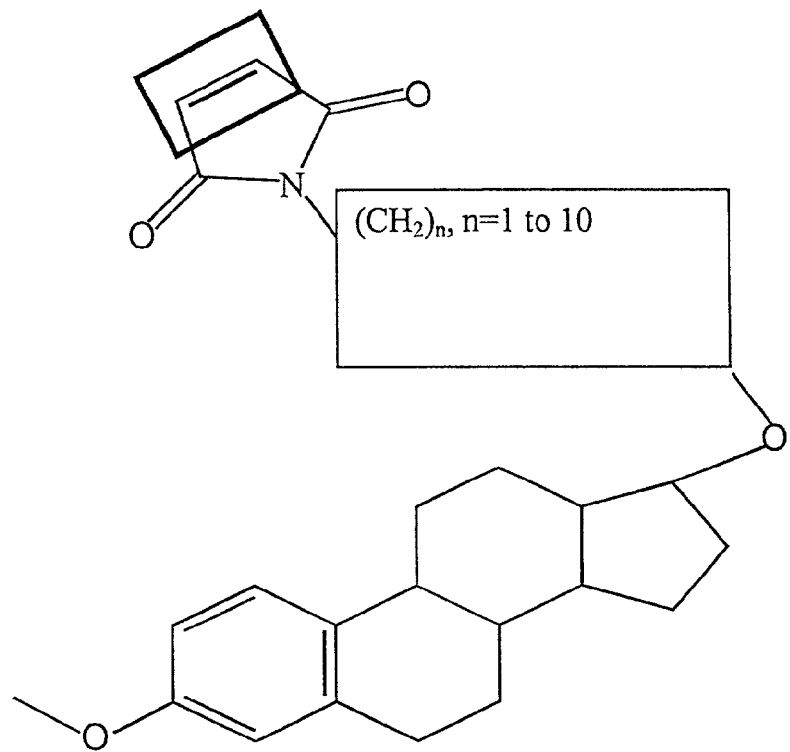
FIG. 2B is a structural formula, Formula 2, for the specific PLC inhibitor U-73, 122, 1-[6-[[(17 beta)-3-methoxyestra-1,3,5(10)-trien-17-yl]amino]hexyl]-)1H-pyrrole-2,5-dione, and its inactive analogue, U-73,343, 1-[6-[[(17 beta)-3-methoxyestra-1,3,5(10)-trien-17-yl]amino]hexyl]-)-2,5-pyrrolidinedione. U-73,122 contains a double bond enclosed within the box, while U-73,343 contains a single bond instead of the double bond.

Preferred N-alkylsuccinimido derivatives of steroids include a structure of the Formula 1 as set forth in FIG. 2B. Preferably, R1 is a methylene chain ranging from one to ten methylene groups, i.e. 1, 2, 3, 4, 5, 6, 7, 8, 9 or 10 methylene groups and R2 is selected from the group including but not limited to —OCH₃, —OH and H.

Other PLC inhibitor compositions that can be employed in accordance with the present invention include the liposome compositions disclosed in U.S. Pat. No. 5,942,246 issued to Mayhue et al. on Aug. 24, 1999; the hispidospermidin composition disclosed in U.S. Pat. No. 5,430,050 issued to Smith et al. on Jul. 4, 1995; and the PLC inhibiting peptides disclosed in U.S. Pat. No. 5,580,956 issued to Saito et al. on Dec. 3, 1996, each of which is herein incorporated by reference in its entirety. Other suitable phospholipase inhibitors include the alphahydroxy phosphonate compounds disclosed in U.S. Pat. No. 5,519,163 to Gibbs et al. issued May 21, 1996, herein incorporated by reference in its entirety.

E. PHARMACEUTICAL FORMULATIONS

In accordance with the present invention, the agents and substances that inhibit PLC biological activity, also referred to herein as "PLC inhibitors", are adapted for administration as a pharmaceutical composition. A preferred pharmaceutical composition comprises a hydrophilic drug; an effective amount of a PLC inhibitor; and a pharmaceutically acceptable carrier.

More preferably, the PLC inhibitor is selected from the group including but not limited to an alkylphosphocholine, a 3-nitrocoumarin, other 3-substituted coumarins indicated in the footnote to Table 1, and an N-alklylsuccinimido steroid derivative. Optionally, the alkylphosphocholine can further comprise an alkyl chain of ten to twenty methylene groups, i.e. an alkyl chain of 10, 11, 12, 13, 14, 15, 16, 17, 18, 19, or 20 methylene groups.

A method of preparing a composition that facilitates oral bioavailability of a hydrophilic drug to a subject in need thereof is also provided. In a preferred embodiment, the method comprises: providing a hydrophilic drug; providing an effective amount of a PLC inhibitor; and mixing the hydrophilic drug and the effective amount of the PLC inhibitor with a pharmaceutically acceptable carrier, whereby a composition that facilitates oral bioavailability of the hydrophilic drug is prepared.

More preferably, the PLC inhibitor is selected from the group including but not limited to an alkylphosphocholine, a 3-nitrocoumarin, and an N-alklylsuccinimido steroid derivative. Even more preferably, the alkylphosphocholine further comprises an alkyl chain of ten to twenty methylene groups, i.e. an alkyl chain of 10, 11, 12, 13, 14, 15, 16, 17, 18, 19, or 20 methylene groups; and N-alkylsuccinimido steroid comprises of alkyl chains of one to ten methylene groups, i.e. an alkyl chain of 1, 2, 3, 4, 5, 6, 7, 8, 9, 10 methylene groups.

Formulation and dose preparation techniques have been generally described in the art, see for example, those described in U.S. Pat. No. 5,326,902 issued to Seipp et al. on Jul. 5, 1994, U.S. Pat. No. 5,234,933 issued to Marnett et al. on Aug. 10, 1993, and PCT Publication WO 93/25521 of Johnson et al. published Dec. 23, 1993, and each of which is herein incorporated by reference in its entirety.

For the purposes described above, the identified substances can normally be administered systemically or partially, usually by oral or parenteral administration. The doses to be administered are determined depending upon age, body weight, symptom, the desired paracellular permeability enhancing effect, the route of administration, and the duration of the treatment, etc. One of skill in the art of therapeutic treatment will recognize appropriate procedures and techniques for determining the appropriate dosage regimen for effective therapy. Additional guidance is also provided by the Laboratory Examples set forth herein below. Various compositions and forms of administration are provided and are generally known in the art. Other compositions for administration include suppositories that comprise one or more of the active substance(s) and can be prepared by known methods.

Thus, a pharmaceutical composition in accordance with the present invention can be formulated with one or more physiologically acceptable carriers or excipients. Thus, the compounds for use according to the present invention can be formulated for oral, buccal, parenteral, rectal or transdermal administration, administration in a form suitable to contact colonic epithelium, or administration in a form suitable for inhalation or insufflation (either through the mouth or the nose) so as to contact, for example, pulmonary alveolar epithelium. Administration can also be accomplished by any other effective techniques.

For oral administration, the pharmaceutical compositions can take the form of, for example, tablets or capsules prepared by a conventional technique with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets can be coated by methods well known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The methods of administration according to the present invention can include parenteral administration by injection, for example by bolus injection or continuous infusion. Formulations for injection can be presented in unit dosage form, e.g., in ampoules or in multi-dose containers, with or without an added preservative. An injectable formulation is particularly contemplated for use in delivering a therapeutic agent across the blood brain barrier to the central nervous system.

The compositions used in the methods can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g. sterile pyrogen-free water, before use. The compounds can also be formulated in rectal compositions such as suppositories or retention enemas, e.g. containing conventional suppository bases such as cocoa butter or other glycerides. In addition to the formulations described previously, the compounds can also be formulated as a preparation for implantation or injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Materials and Methods for Laboratory Examples

Reagents

MDCK epithelial cell line strain II was obtained from the American Type Culture Collection through the Lineberger Comprehensive Cancer Center (University of North Carolina (UNC) at Chapel Hill, Chapel Hill, N.C.). N-2-hydroxyethylpiperazine-N'-2-ethansulfonic acid (HEPES) was obtained from Lineberger Comprehensive Cancer Center (UNC at Chapel Hill). Hank's Balanced Salt Solution (HBSS) was obtained from Mediatech of Hernford, Va. Cell culture reagents were obtained from Gibco BRL of Grand Island, N.Y. TRANSWELL™ multi-well plates and inserts (12 wells/plate, 3 μm pore and 1.0 cm$^2$ area, polycarbonate) were obtained from Costar of Cambridge, Mass. [$^{14}$C]-mannitol and [$^3$H]-myo-inositol were obtained from American Radiolabeled Chemicals of St. Louis, Mo. Dodecylphosphocholine was obtained from Avanti Polar Lipids of Alabaster, Ala. AG1-X8 formate columns were obtained from Bio-Rad Laboratories of Hercules, Calif. All other compounds and reagents were obtained from Sigma Chemical Company, St. Louis, Mo.

Cell Culture

For transport studies, MDCK cells, derived from normal proximal epithelial kidney cells of a male cocker spaniel, which is model for transport experiments (Cho, M. J., et al. (1989) *Pharm. Res.* 6:71-77), were grown on TRANSWELL™ multi-well plates. Each well was seeded with 200,000 cells. The cells were then grown in cell media (MEM with 1% antibiotic, supplemented with 10% fetal bovine serum (FBS) and 1% NEAA), and were maintained at 37° C. and 5% $CO_2$. Confluent cells were grown for four days where they differentiated into epithelial cell monolayers as evidenced by the establishment of a stable TEER.

Measurement of Transepithelial Electrical Resistance (TEER).

TEER (expressed as $\Omega \cdot cm^2$) serves as a measure of functional integrity of tight junctions. TEER was measured by an EVOM Epithelial Tissue Voltohmeter (World Precision Instruments, Sarasota, Fla.) and an Endohm-12 electrode (World Precision Instruments, Sarasota, Fla.). TEER values of MDCK cells that formed a functional monolayer ranged between 150-250 $\Omega \cdot cm^2$.

Mannitol as a Paracellular Marker

Mannitol, a hydrophilic compound, cannot readily cross the epithelial membrane, and must transverse the epithelium via the paracellular pathway. Therefore, the flux of mannitol through the epithelium is a reflection of the permeability of the paracellular pathway. Detection of mannitol is accomplished with [$^3$H] or [$^{14}$C] radiolabels.

Determination of the Effect of Alkylphosphocholines on TEER.

Experiments were initiated by adding 0.5 mL of HBSS supplemented with 10 mM HEPES, pH 7.4 (transport buffer) containing compound or vehicle to the apical side of the TRANSWELL™ multi-well plate. Cell monolayers were incubated at 37° C. and TEER values were measured after 30 minutes. Data from each experiment were normalized to the response from the vehicle and were reported as the mean±SD of three experiments performed in triplicate.

The effect of akylphosphocholines on TEER was evaluated at several concentrations, and the concentration that caused a 50% decrease in TEER with respect to the untreated control was defined as $EC_{50}$ (Liu, D. Z., et al. (1999) *J. Pharm. Sci.* 88:1161-1168; Liu, D. Z., et al. (1999) *J. Pharm. Sci.* 88:1169-1174).

Determination the Effect of Alkylphosphocholines on Mannitol Transport.

The integrity of the tight junctions of cell monolayers was monitored with the measurement of TEER prior to the experiment. Transport experiments were initiated by replacing the apical media with 0.5 mL of transport buffer containing compound or vehicle, and [$^{14}$C]-mannitol. Concentration of [$^{14}$C]-mannitol was 25 µM (55 mCi/mmol). Transport rates were monitored by the measurement of the amount of [$^{14}$C]-mannitol accumulated in the basolateral side (1.5 mL) during two 30-minute intervals. The amount of radiolabeled [$^{14}$C]-mannitol transported was measured by liquid scintillation counting in a Packard Tri Carb 4000 Series spectrophotometer available from Packard Instrument Company of Meriden, Conn. All transport experiments were carried out under sink conditions (transport experiments were designed such that less than 10% of the total amount of [$^{14}$C]-mannitol was present on the basolateral side at any given time). The effect of alkylphosphocholines on the transport of [$^{14}$C]-mannitol was normalized to the transport of [$^{14}$C]-mannitol in the vehicle-treated cells and was reported as the mean±SD of three experiments performed in triplicate. The $EC_{10x}$ was determined by the concentration of compound that causes a 10-fold increase in mannitol flux with respect to the vehicle treated control.

Determination of PLC Activity by Cellular Assay

Measurement of activity of PLC in MDCK cells was determined by an adaptation of a previously published method (Schachter, J. B., et al. (1997) *Neuropharm.* 36:1181-1187). MDCK cells were seeded at 400,000 cells/well in a 12-well plate and subsequently cultured for four days. MDCK cell monolayers were then labeled with [$^3$H]-myo-inositol (1.6 µCi/well in 0.4 ml of inositol-free media) for 24 hours at 37° C. Assays were initiated on labeled cells that were removed from the incubator by immediately supplementing the cells with 100 µl of 250 mM HEPES (pH 7.3), containing 100 mM LiCl with or without compound. Subsequently, the cells were incubated for 30 minutes at 37° C. Immediately after the termination of this incubation, ATP (final concentration: 100 µM) or EGF (20 ng/ml) was added.

The cells were then incubated at 37° C. for 15 minutes to allow accumulation of [$^3$H]-inositol phosphates. Incubations were terminated by aspiration of the media and the addition of 1 ml of boiling 10 mM EDTA (pH 8.0). The supernatant was applied to AG1 X8 formate columns for chromatographic isolation of [$^3$H]-inositol phosphates (Berridge, M. J., et al. (1983) *Biochem. J.* 212:473-482). The amount of [$^3$H]-inositol phosphates was measured by liquid scintillation counting in a Packard Tri Carb 4000 Series spectrophotometer. Data from each experiment were normalized to the response observed with 100 µM ATP or 20 ng/ml EGF and were reported as the mean±SD of three experiments performed in triplicate. The $IC_{50}$ (PLC) was determined by the concentration of compound that causes a 50% decrease in ATP- or EGF-stimulated accumulation of [$^3$H]-inositol phosphates.

Synthesis of Alkylphosphocholines that Differ in Alkyl Chain Length

Alkylphosphocholines were synthesized via phosphorylation of alcohol with 2-bromoethyl-dichlorophosphate (Hirt, R., and Berchtold, R. (1958) *Pharma. Acta. Helv.* 33:349-356), followed by substitution of bromine with trimethylamine (Hanson, W. J., et al. (1982) *Lipids* 17:453-459; Surles, J. R., et al. (1993) *Lipids* 28:55-57).

Data Analysis

The Student t-test for unpaired data was used to determine significant differences ($p<0.05$) between the mean±SD from untreated and treated MDCK cell monolayers. The relation between PLC activity and increase in paracellular permeability was examined by linear regression analysis, and the correlation was expressed by the Pearson correlation coefficient.

Laboratory Example 1

Effect of Alkylphosphocholines on TEER Across MDCK Cells

The effect of alkylphosphocholines on TEER was evaluated from a 10-minute and 30-minute treatment of the MDCK cell monolayers. After 10 minutes, most compounds (at non-toxic concentrations) in the alkylphosphocholine series did not significantly ($p>0.05$) decrease TEER. After 30 minutes, all alkylphosphocholines decreased TEER in a concentration-dependent manner (FIG. 3—for clarity, only C12 and C16 compounds in this series are shown). For example, the effect of 30 µM C16 on TEER is delayed for 10 minutes, then TEER drops consistently over a two-hour period to less than 10% of control values (insert in FIG. 3). To avoid potential nonspecific effects from long-term treatments with alkylphosphocholines, the shortest treatment time (i.e., the 30-minute treatment) that caused a significant increase in paracellular permeability was chosen for further experiments.

Figure 3:
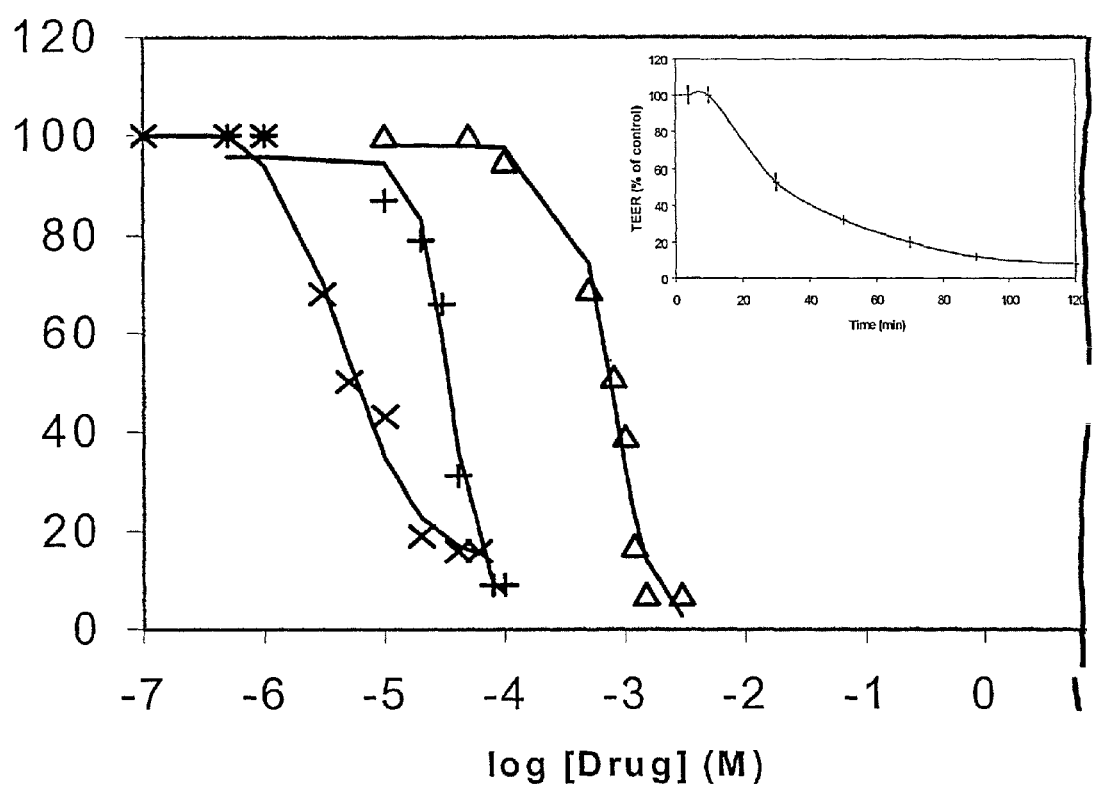
FIG. 3 is a graph depicting the effect of alkylphosphocholines and U-73,122 on TEER in MDCK cells. Compounds were administered apically. TEER was measured after 30-minute incubation with the compound at 37° C. Data points represent mean±SD (n=3). Symbols that represent the compounds are ΔC12, +C16, and X U-73,122. The insert is the effect of the time of treatment of 30 µM C16 on TEER across MDCK monolayers.

All alkylphosphocholines in this series decreased TEER in a concentration-dependent manner, such that, at maximum concentrations, all alkylphosphocholines decreased TEER less than 20% of control values (FIG. 3). The potency of alkylphosphocholines, which corresponded to the concentration of alkylphosphocholines that decreased TEER by 50% ($EC_{50}$), varied markedly (Table 2). Interestingly, small variations in the alkyl chain produced significant ($p<0.05$) changes in the $EC_{50}$ of these compounds. For example, C16 and C12 differ by four methylene units in their alkyl chain, but their respective $EC_{50}$ values differ by approximately 25-fold. To confirm that alkylphosphocholines increase paracellular permeability across MDCK cell monolayers, the ability of alkylphosphocholines to increase mannitol flux was then determined.

Laboratory Example 2

Effect of Alkylphosphocholines on Mannitol Flux Across MDCK Cells

The influence of alkylphosphocholines on mannitol flux across MDCK cell monolayers was also monitored as a function of time. Treatment of these compounds for less than 30 minutes did not significantly ($p<0.05$) increase mannitol flux across MDCK cell monolayers. This result corresponds to the preferred step of a treatment with alkylphosphocholines for a pre-determined time (e.g. a 30-minute treatment) before TEER significantly ($p<0.05$) decreases across MDCK cell monolayers. Therefore, measurement of mannitol flux was immediately initiated after a 30-minute alkylphosphocholine treatment and immediately terminated before a 60-minute alkylphosphocholine treatment (i.e., measurement spanned an interval between 30 and 60 minutes).

Figure 4:
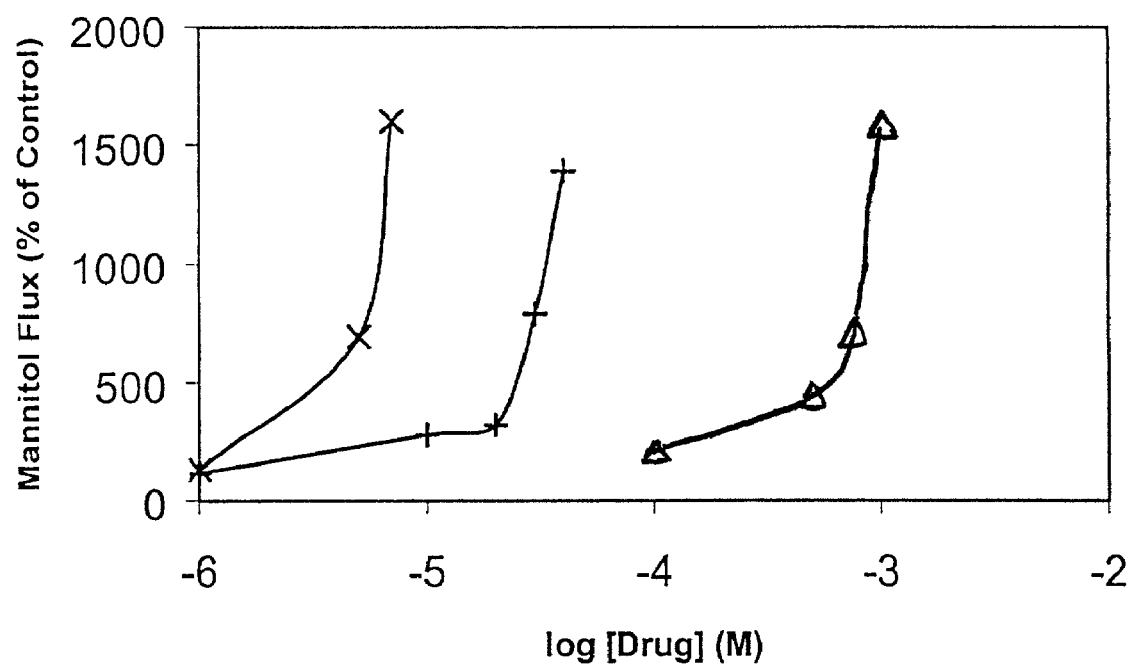
FIG. 4 is a graph depicting the effect of alkylphosphocholines and U-73,122 on mannitol flux in MDCK cells. Compounds and [$^{14}$C]-mannitol were administered apically. Transport rates were monitored by measuring the amount of [$^{14}$C]-mannitol accumulated in the basolateral side (1.5 mL) during the interval between 30- and 60-minute treatment with compound or vehicle. Data points represent mean±SD (n=3). Symbols that represent the compounds are ΔC12, +C16, and X U-73,122.

Alkylphosphocholines increased mannitol flux in a concentration-dependent manner (FIG. 4, for clarity only C12 and C16 compounds in this series are shown). The maximum effect of these compounds on mannitol permeability could not be obtained because at high concentrations, alkylphosphocholines did not produce saturable response. Therefore, the ability of these compounds to increase paracellular permeability was compared by the concentration of compound that increased mannitol flux by 10-fold ($EC_{10x}$) (Liu, D. Z., et al. (1999) *J. Pharm. Sci.* 88:1161-1168; Liu, D. Z., et al. (1999) *J. Pharm. Sci.* 88:1169-1174).

The 10-fold increase in mannitol flux over the control value corresponds to 50% of the maximal mannitol flux obtained with EDTA (Liu, D. Z., et al. (1999) *J. Pharm. Sci.* 88:1169-1174). The $EC_{10x}$ of alkylphosphocholines is summarized in Table 2. The $EC_{10x}$ of these compounds corresponded well with the $EC_{50}$ values attained for alkylphosphocholines.

Laboratory Example 3

Effect of Alkylphosphocholines on PLC Activity in MDCK Cells

To determine the ability alkylphosphocholines to inhibit PLC activity, the ability of these compounds to inhibit the ATP-mediated increases in the levels of inositol phosphates was determined. The separation between the counts from basal and ATP-stimulated levels of [$^3$H]-inositol-phosphates from MDCK cell monolayers was, however, marginal (approximately 1.5-fold) for a reliable determination of the ability of alkylphosphocholines to inhibit PLC activity. To increase this separation, MDCK cells that were transfected with a plasmid that encoded the $P2Y_2$ receptor were employed. The $P2Y_2$ receptor is G-protein coupled receptor that activates PLC (Pawelczyk, T., and Lowenstein, J. M. (1993) *Biochem. Pharm.* 45:493-497). The separation between the counts from basal and ATP-stimulated levels of [$^3$H]-inositol-phosphates from MDCK monolayers that express $P2Y_2$ receptors increased to approximately a 3-fold difference (counts from basal and ATP-stimulated levels of [$^3$H]-inositol-phosphates ranged from 200 to 400 and 700 to 1200 cpm, respectively).

Figure 5:
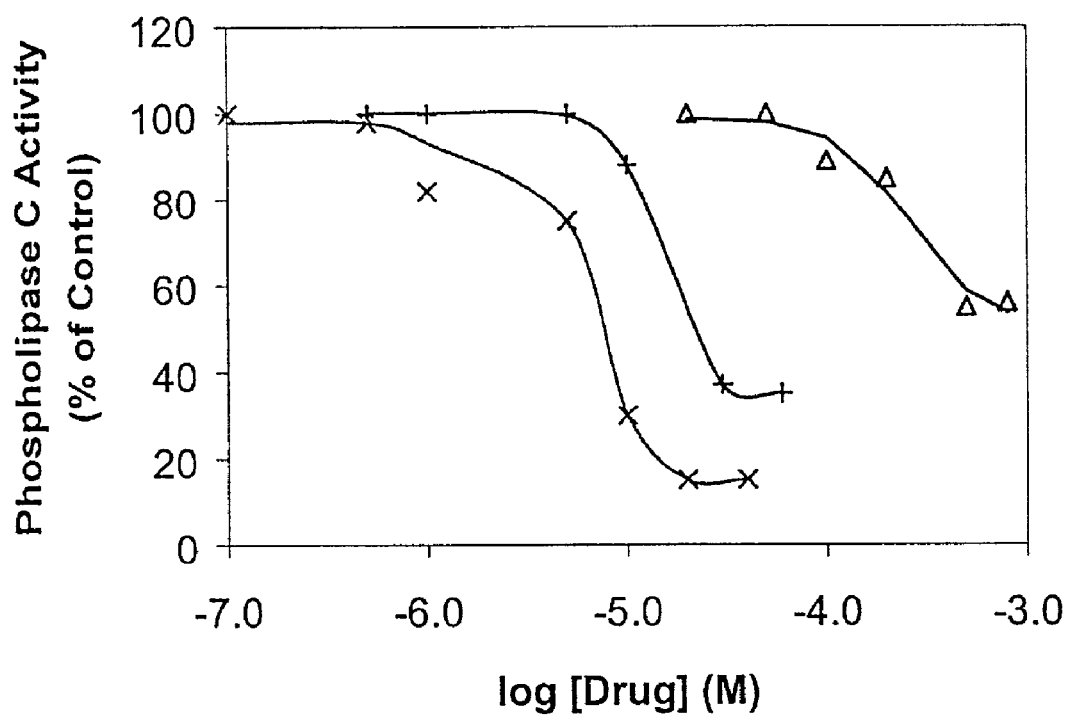
FIG. 5 is a graph depicting the effect of alkylphosphocholines and U-73,122 on ATP-stimulated PLC activity in MDCK cells. MDCK monolayers were labeled with [$^3$H]-myo-inositol for 24 hours at 37° C. MDCK cells were then treated with compound for 30 minutes at 37° C. Inositol phosphate production was stimulated with 100 µM ATP for 15 minutes. [$^3$H]-inositol phosphates were isolated by chromatography. The amount of [$^3$H]-inositol phosphates was then measured by liquid scintillation counting in a Packard Tri Carb 4000 Series spectrophotometer available from Packard Instrument Company of Meriden, Conn. Data points represent mean±SD (n=3). Symbols that represent the compounds are ΔC12, +C16, and X U-73,122.

To determine whether PLC inhibition is associated with the ability of alkylphosphocholines to increase paracellular permeability in MDCK cells, the ability of alkylphosphocholines to decrease ATP-stimulated increase in inositol phosphate production was also measured (FIG. 5, for clarity only C12 and C6 compound in this series are shown). The potency of alkylphosphocholines, which corresponded to the concentration of alkylphosphocholines that inhibited PLC activity by 50% ($IC_{50}$ (PLC)), varied (Table 2). The full extent of PLC inhibition from these compounds also varied. For example, C10, the least potent enhancer of paracellular permeability in this series, is not included in Table 2 because C10 could not reduce ATP-stimulated increase in inositol phosphate production by 50%. Furthermore, the full extent of PLC inhibition from treatment with C12 was 50%. This result is not surprising since C10 and C12 are the least potent enhancers of paracellular permeability in this series.

Figure 6:
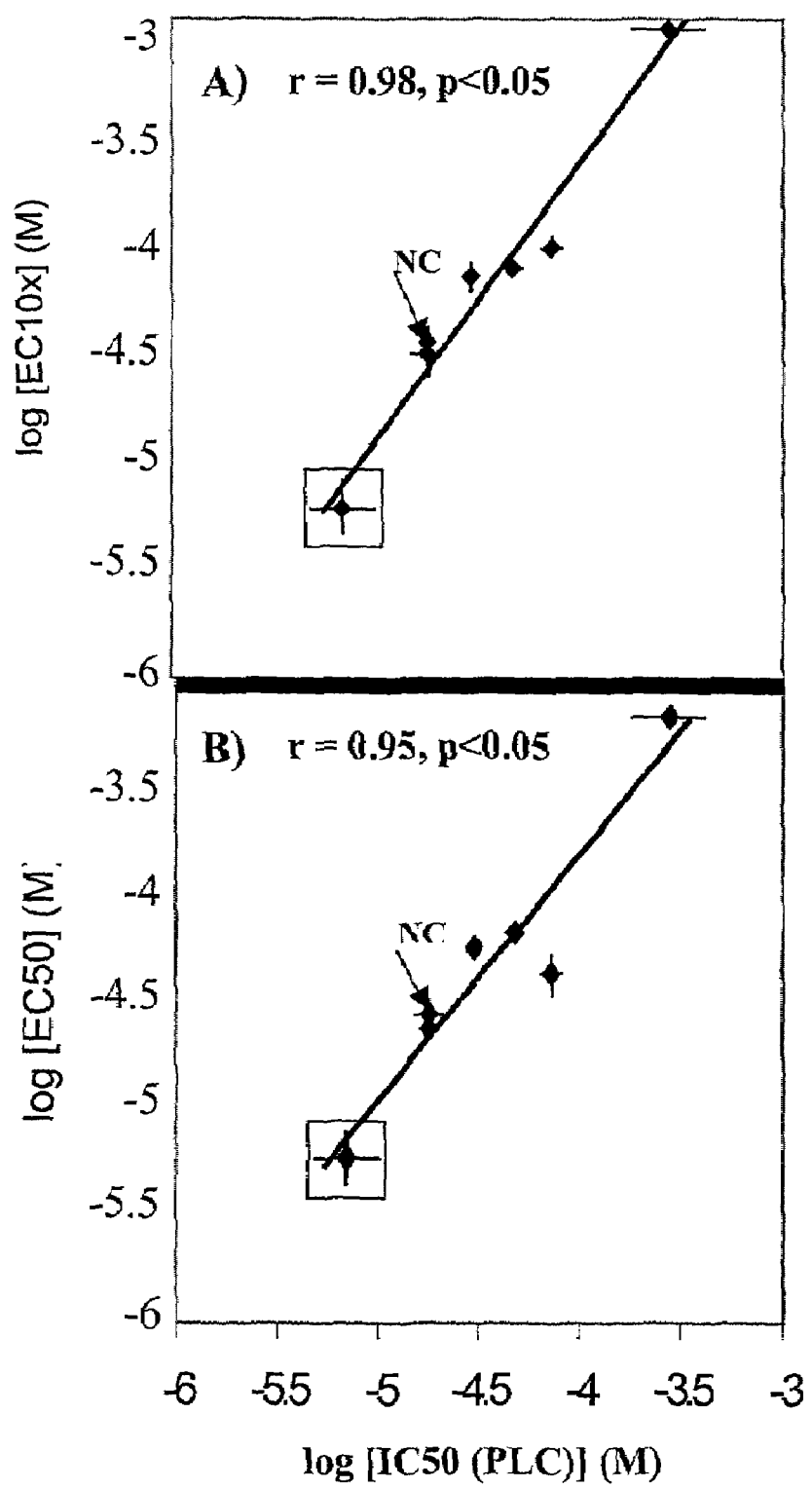
FIG. 6A is a graph depicting the correlation (r=0.98, p<0.05) between the IC$_{50}$ (PLC) and EC$_{10x}$ values for alkylphosphocholines, 3-NC, and U-73,122. The data point enclosed in the box represents U-73,122, and the data point for 3-NC is labeled as NC.
FIG. 6B is a graph depicting the correlation (r=0.95, p<0.05) between the IC$_{50}$ (PLC) and EC$_{50}$ values for alkylphosphocholines, 3-NC, and U-73,122. Data points represent mean±SD in triplicate for three experiments. The data point enclosed in the box represents U-73,122, and the data point for 3-NC is labeled as NC.

Whether the ability of alkylphosphocholines to increase paracellular permeability (i.e., $EC_{10x}$ and $EC_{50}$) correlated with their ability to inhibit PLC (i.e., $IC_{50}$ (PLC)) was also determined. In general, alkylphosphocholines that were less potent enhancers of paracellular permeability were also less potent inhibitors of PLC (Table 2). This observation was confirmed by the determination of a significant ($p<0.001$) positive correlation between $EC_{10x}$ and $IC_{50}$ (PLC) (FIG. 6A) and $EC_{50}$ and $IC_{50}$ (PLC) (FIG. 6B). Data points did not markedly vary from either of these correlations ($r>0.94$ for both correlations). Therefore, these correlations indicate that the ability of alkylphosphocholines to increase paracellular permeability is associated with the ability of these compounds to inhibit PLC activity.

As the alkylphosphocholines become less potent, the separation between their potency of paracellular enhancement (i.e., $EC_{50}$ and $EC_{10x}$) and PLC inhibition (i.e., $IC_{50}$ (PLC)) becomes larger (Table 2). For example, the $IC_{50}$ (PLC) and $EC_{10x}$ for C16, the most potent enhancer in the alkylphosphocholine series, differ marginally, whereas the $IC_{50}$ and $EC_{10x}$ for C12, one of the least potent enhancers in the alkylphosphocholine series, differ markedly (Table 2). This relationship is also illustrated in the correlations between $IC_{50}$ (PLC) and $EC_{10x}$, and $IC_{50}$ (PLC) and $EC_{50}$, where these correlations are linear on log-log scale. Therefore, these correlations indicate that the ability of the less potent enhancers to increase paracellular permeability become less dependent on the ability of the enhancer to inhibit PLC and more dependent on other nonspecific effects (i.e., lytic effects on the cell membrane and reduced cell viability).

Laboratory Example 4

Effect of Structurally Unrelated PLC Inhibitors on Paracellular Permeability Across MDCK Cells To further establish whether increased paracellular permeability is the result of PLC inhibition, the ability of a selective PLC inhibitors (e.g., U-73,122 and 3-nitrocoumarin) (see FIGS. 7A and 7B for structures, respectively) to increase paracellular permeability was determined. The ability of these selective PLC inhibitors to increase paracellular permeability has not previously been shown. Whether U-73,122 and 3-nitrocoumarin would significantly ($p<0.05$) correlate with the ability of alkylphosphocholines to inhibit PLC and increase paracellular permeability in MDCK cell monolayers was also determined.

Figure 7:
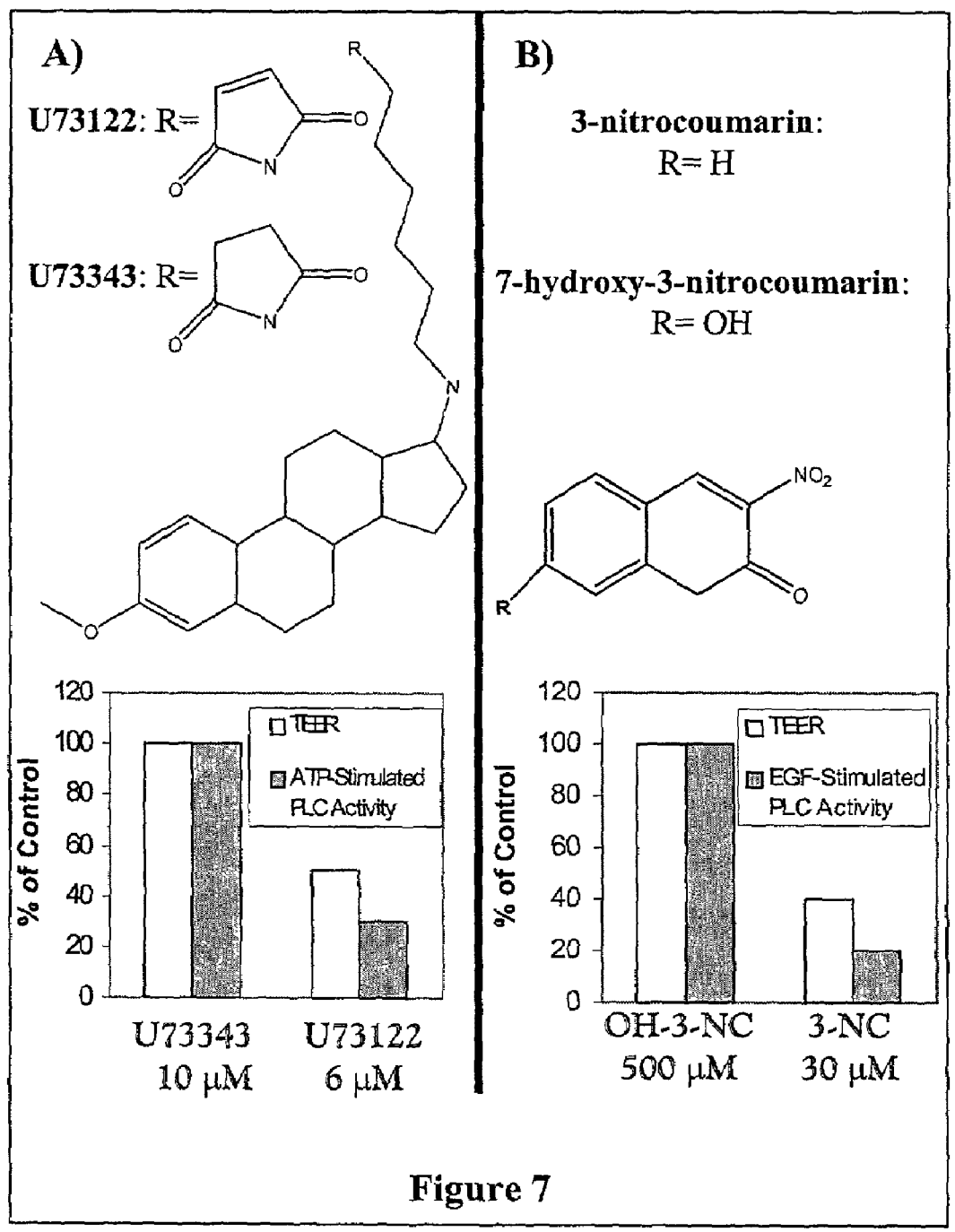
FIG. 7A is a structural formula and a bar graph depicting the effect of U-73,122 and U-73,343 on TEER (open bar) and ATP-stimulated PLC activity (shaded bar).
FIG. 7B is a structural formula and a bar graph depicting the effect of 3-nitrocoumarin and 7-hyroxy-3-nitrocoumarin on TEER (open bar) and EGF-stimulated PLC activity (shaded bar).

To ensure that the increase in paracellular permeability is dependent on PLC inhibition, the ability of selective PLC inhibitor, U-73,122 (Bleasdale, J. E., et al. (1989) *Adv. Prostaglandin Thromboxane Leukot. Res.* 19:590-593), to decrease TEER and increase mannitol flux was determined. U-73,122 potently decreased TEER and increased mannitol flux across MDCK monolayers (FIG. 3, FIG. 4, and Table 2). On the other hand, the negative control compound, U-73,343, did not decrease TEER or ATP-stimulated PLC activity (FIG. 7A). This difference in activity between these two compounds is remarkable considering they differ in structure by one double bond (FIG. 2B). To the knowledge of the present co-inventors, U-73,122 is the one of the most potent enhancers of paracellular permeability. Further, the ability of another structurally unrelated inhibitor of PLC, 3-nitrocoumarin, to increase paracellular permeability has also been demonstrated. It is approximately as potent as C16 alkylphosphocholine, with respect to inhibition of PLC ($IC_{50}$ (PLC)) and enhancement of paracellular permeability ($EC_{50}$ and $EC_{10x}$) (Table 2). This result confirms that PLC inhibition is associated with the increase in paracellular permeability in MDCK cells.

Finally, whether the ability of U-73,122 and 3-nitrocoumarin to increase paracellular permeability and inhibit PLC would correlate with ability of alkylphosphocholines to alter these parameters was determined. Previously reported concentrations of U-73,122 (Lockhart, L. K., and McNicol, A. J. (1999) *Pharm. Exp. Ther.* 289:721-728) inhibited PLC activity by 50% in MDCK cells (FIG. 5 and Table 2). The $EC_{50}$ and $EC_{10x}$, and $IC_{50}$ (PLC) values for U-73,122 and 3-nitrocoumarin significantly (p<0.05) correlated with these values for alkylphosphocholines (FIGS. 6A and 6B). This evidence establishes the involvement of PLC in the regulation of paracellular permeability.

TABLE 2

Summary of $EC_{50}$, $EC_{10x}$ and $IC_{50}$ (PLC) Values for Alkylphosphocholines, 3-Nitrocoumarin, and U-73, 122 in MDCK Cells*

| | $EC_{50}$ (µM) | $EC_{10x}$ (µM) | $IC_{50}$(PLC) (µM) |
|---|---|---|---|
| U-73, 122 | 6 ± 2 | 6 ± 2 | 7 ± 3 |
| 3-nitrocoumarin | 24 ± 1 | 34 ± 5 | 21 ± 5 |
| C12 | 733 ± 32 | 900 ± 100 | 275 ± 135 |
| C14 | 44 ± 11 | 91 ± 11 | 73 ± 9 |
| C16 | 29 ± 5 | 30 ± 8 | 36 ± 18 |
| C18 | 59 ± 8 | 66 ± 11 | 30 ± 2 |
| C20 | 71 ± 8 | 73 ± 1 | 48 ± 5 |

*Results are reported as mean ± SD in triplicate for three experiments.

Laboratory Example 5

Isozyme Family-Selective Inhibition of PLC-γ by U73122 and HPC

Figure 8:
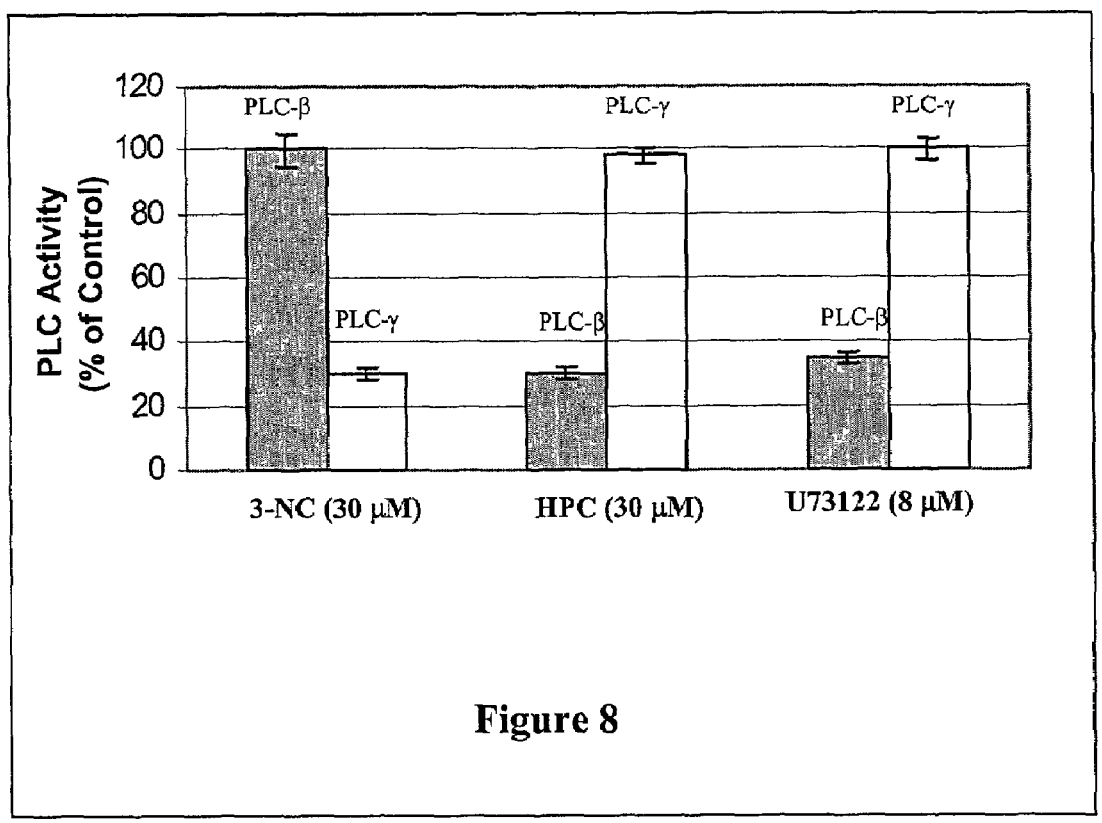
FIG. 8 is a bar graph depicting the effect of 3-NC, HPC or U-73,122 on PLC-β (shaded bars) and PLC-γ (open bars) activity. MDCK monolayers were labeled with [$^3$H]-myo-inositol for 24 hours at 37° C. MDCK cells were then treated with 3-NC, HPC or U-73,122 for 30 minutes at 37° C. Inositol phosphate production was stimulated with 100 µM ATP or 20 ng/ml EGF for 15 minutes to activate PLC-β and -γ activity, respectively. [$^3$H]-inositol phosphates were isolated by chromatography. The amount of [H$^3$]-inositol phosphates was then measured by liquid scintillation counting in a Packard Tri Carb 4000 Series spectrophotometer.

U-73,122 has been previously reported to selectively inhibit PLC isozyme family-β (Thompson et al. 1991). The present disclosure also indicates that HPC is an inhibitor of PLC-γ by the fact that HPC was a potent inhibitor of ATP-stimulated PLC-β activity (FIG. 5). Hence, in this Example, the selectivity of HPC and U-73,122 for PLC-β versus another PLC isozyme, PLC-γ, was determined. U-73,122 and HPC inhibited ATP-stimulated PLC-β activity; however, had no effect on EGF-stimulated PLC-γ activity (FIG. 8). As previously described, these compounds are potent enhancers of the tight junction permeability across MDCK cell monolayers. Therefore, inhibition of PLC-β is associated with the increase in tight junction permeability across MDCK cell monolayers.

Laboratory Example 6

Isozyme Family-Selective Inhibition of PLC-γ is Associated with Increased Tight Junction Permeability In this Example, a known inhibitor of PLC-γ, 3-nitrocoumarin (3-NC) (Perrella et al., *Journal of Medicinal Chemistry* (1994) 37 (14):2232-2237) was found to be a selective inhibitor of PLC-γ, with no inhibitory activity toward PLC-β in the MDCK cell monolayers (FIG. 8). This compound increased tight junction permeability and inhibited EGF-stimulated PLC-γ activity (FIG. 7B), suggesting that inhibition of PLC-γ is also associated with increased tight junction permeability. The structurally similar analog of 3-NC, 7-hydroxy-3-nitrocoumarin (OH-3-NC) (FIG. 7B), which has been previously reported not to inhibit PLC (Perrella et al., *Journal of Medicinal Chemistry* (1994) 37 (14):2232-2237), did not increase tight junction permeability even at 500 µM concentration (FIG. 7B), suggesting that the ability of 3-NC to increase tight junction permeability is through inhibition of PLC-γ.

The evidence of the involvement of the PLC-dependent pathway in the regulation of paracellular permeability is growing. But, the disclosure of the present invention is the first to establish a direct association between PLC inhibition and paracellular permeability. Furthermore, one of the most potent enhancers of paracellular permeability (i.e., U-73,122) was identified. Thus, the present invention provides an elucidation of the mechanism behind the ability of agents to increase paracellular permeability and has generated new insight into the regulation of the tight junction.

REFERENCES

The references listed below as well as all references cited in the specification are incorporated herein by reference to the extent that they supplement, explain, provide a background for or teach methodology, techniques and/or compositions employed herein.

Anderson, J. M., et al. (1998) *J. Cell Biol.* 106:1141-1149.
Anderson, J. M., and Van Itallie, C. M. (1995) *Am. J. Phys.* 269:G467-G475.
Ballard, S. T., et al. (1995) *Annu. Rev. Nutr.* 15:35-55.
Berkovic, D., et al. (1996) *J. Exp. Ther. Onc.* 1:302-311.
Berridge, M. J., et al. (1983) *Biochem. J.* 212:473-482
Bleasdale, J. E., et al. (1989) *Adv. Prostaglandin Thromboxane Leukot. Res.* 19:590-593.
Cho, M. J., et al. (1989) *Pharm. Res.* 6:71-77.
Citi, S., and Kendrick-Jones, J. (1987) *BioEssays* 7:155-159.
Collares-Buzato, C. B., et al. (1998) *Eur. J. Cell Biol.* 76:85-92.
Denkar, B. M., and Nigam, S. K. (1998) *Am. J. Physiol.* 274:F1-F9.
Diamond, J. (1977) "The epithelial junction: bridge, gate and fence", *Physiologist* 20:10-18.
Fanning, A. S., et al. (1999) *J. Soc. Nephrol.* 10:1337-1345.
Hanson, W. J., et al. (1982) *Lipids* 17:453-459
Hecht, G., et al. (1996) *Am. J. Phys.* 271:C1678-C1684.
Hirt, R., and Berchtold, R. (1958) *Pharma. Acta. Helv.* 33:349-356
Keller, T. C. S., and Mooseker, M. S. (1982) *J. Cell Biol.* 95:943-959.
Lindmark, T., et al. (1998) *J. Pharm. Exp. Ther.* 284:362-369.
Liu, D. Z., et al. (1999) *J. Pharm. Sci.* 88:1169-1174.
Liu, W. S., and Heckman, C. A. (1998) *Cell. Signal.* 10:529-542.
Liu, D. Z., et al. (1999) *J. Pharm. Sci.* 88:1161-1168.
Lockhart, L. K., and McNicol, A. J. (1999) *Pharm. Exp. Ther.* 289:721-728.
Mullin, J. M., et al. (1998) *Am. J. Physiol.* 275:C544-C554.
Nicholas, R. A., et al. (1996) *Mol Pharmacol.* 50:224-229.
Pawelczyk, T., and Lowenstein, J. M. (1993) *Biochem. Pharm.* 45:493-497.
Perrella et al., *Journal of Medicinal Chemistry* (1994) 37 (14):2232-2237.
Sakakibara, A., et al. (1997) *J. Cell Biol.* 137:1393-1401.
Schachter, J. B., et al. (1997) *Neuropharm.* 36:1181-1187.
Surles, J. R., et al. (1993) *Lipids* 28:55-57.
Tai, Y. H., et al. (1996) *J. Membr. Biol.* 149:71-79.
Tkachuk, V. A. (1998) *Biochemistry (Mosc).* 63:38-46.
Tomita, M., et al. (1995) *Pharm. Exp. Ther.* 272:739-743.
Turner, J. R., et al. (1997) *Am. J. Physiol.* 273:C1378-C1385
Winter, M. C., et al. (1991) *Am. J. Respir. Cell Mol. Biol.* 4:470-477.
U.S. Pat. No. 5,942,246
U.S. Pat. No. 5,430,050
U.S. Pat. No. 5,580,956
U.S. Pat. No. 5,519,163

U.S. Pat. No. 5,208,223
U.S. Pat. No. 5,144,045
U.S. Pat. No. 5,326,902
U.S. Pat. No. 5,234,933
PCT Publication WO 93/25521.

It will be understood that various details of the invention can be changed without departing from the scope of the invention. Furthermore, the foregoing description is for the purpose of illustration only, and not for the purpose of limitation—the invention being defined by the claims.

What is claimed is:

1. A method of enhancing paracellular permeability at an absorption site where tight junctions are present in a subject, the method comprising:
   (a) administering an effective amount of a phospholipase C inhibitor to a subject at a time in which enhanced paracellular permeability is desired, wherein the phospholipase C inhibitor comprises a compound having the following structure:

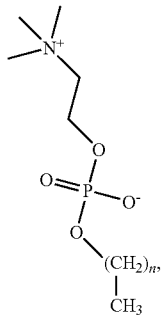

where n=13-19; and
   (b) enhancing paracellular permeability in the subject at the absorption site through the administering of the effective amount of the phospholipase C inhibitor, wherein the absorption site is a site at the intestinal epithelium or at the blood-brain barrier of the subject where tight junctions are present.

2. The method of claim 1, wherein the phospholipase C inhibitor is formulated for oral, buccal, rectal or transdermal administration, or in a form suitable to contact colonic epithelium, or in a form suitable for administration by inhalation or insufflation.

3. A method of enhancing paracellular permeability in the intestinal epithelium where tight junctions are present in a subject, the method comprising:
   (a) administering a composition comprising an effective amount of a phospholipase C inhibitor to a subject at a time in which enhanced paracellular permeability is desired, wherein the phospholipase C inhibitor comprises a compound having the following structure:

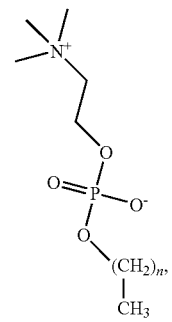

where n=13-19; and
   (b) enhancing paracellular permeability in the subject in the intestinal epithelium through the administering of the effective amount of the phospholipase C inhibitor, wherein the absorption site is a site where tight junctions are present.

4. The method of claim 3, wherein the composition is formulated for oral administration.

5. The method of claim 3, wherein the composition is formulated for parenteral administration.

* * * * *